(12) United States Patent
Choi et al.

(10) Patent No.: US 8,679,804 B2
(45) Date of Patent: Mar. 25, 2014

(54) MODIFIED YEAST STRAIN AND A METHOD FOR PRODUCING SQUALENE USING THE SAME

(75) Inventors: Eui Sung Choi, Daejeon (KR); Jae Ik Whang, Daejeon (KR); Hee Kyoung Ryu, Gyeongsangnam-do (KR); Seon Won Kim, Gyeongsangnam-do (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 23 days.

(21) Appl. No.: 13/460,244

(22) Filed: Apr. 30, 2012

(65) Prior Publication Data

US 2012/0322129 A1   Dec. 20, 2012

Related U.S. Application Data

(63) Continuation-in-part of application No. PCT/KR2010/007621, filed on Nov. 1, 2010.

(30) Foreign Application Priority Data

Oct. 30, 2009   (KR) .................. 10-2009-0104505

(51) Int. Cl.
*C12P 5/02*   (2006.01)
*C12N 1/00*   (2006.01)

(52) U.S. Cl.
USPC ................... 435/167; 435/254.21; 435/254.2; 435/254.11; 435/243

(58) Field of Classification Search
USPC ............. 435/167, 254.21, 254.2, 254.11, 243
See application file for complete search history.

(56) References Cited

U.S. PATENT DOCUMENTS

| | | | |
|---|---|---|---|
| 5,821,038 | A | 10/1998 | Fleer et al. |
| 2003/0092144 | A1 | 5/2003 | Millis et al. |
| 2004/0110257 | A1 | 6/2004 | Millis et al. |
| 2004/0235088 | A1 | 11/2004 | Weber et al. |
| 2006/0275760 | A1* | 12/2006 | Choi et al. .................. 435/6 |
| 2008/0171378 | A1 | 7/2008 | Keasling et al. |

FOREIGN PATENT DOCUMENTS

WO   WO-2008039499 A2   4/2008

OTHER PUBLICATIONS

T. Polakowski et al., "Overexpression of a cytosolic hydroxymethylglutaryl-CoA reductase leads to squalene accumulation in yeast", Appl. Microbiol. Biotechnol.; vol. 49, pp. 66-71 (1998).
C. Arnezeder et al., "Influence of Growth Rate on the Accumulation of Ergosterol in Yeast-Cells", Biotechnology Letters, vol. 12, No. 4, pp. 277-282 (1990).
P. Bhattacharjee et al., "Studies on fermentative production of squalene", World Journal of Microbiology & Biotechnology, vol. 17, pp. 811-816 (2001).
K. Tokuhiro et al., "Overproduction of Geranylgeraniol by Metabolically Engineered *Saccharomyces cerevisiae*", Applied and Environmental Microbiology, vol. 75, No. 17, pp. 5536-5543 (Sep. 2009).
C. Ohto et al., "Overexpression of the gene encoding HMG-CoA reductase in *Saccharomyces cerevisiae* for production of prenyl alcohols", Apppl. Microbiol. Biotechnol, vol. 82, pp. 837-845 (2009).
K. Allen G. Donald, "Effects of Overproduction of the Catalytic Domain of 3-Hydroxy-3-Methylglutaryl Coenzyme A Reductase on Squalene Synthesis in *Saccharomyces cerevisiae*", Applied and Environmental Microbiology, vol. 63, No. 9, pp. 3341-3344 (Sep. 1997).
N. Kamimura et al., "Construction of squalene-accumulating *Saccharomyces cerevisiae* mutants by gene disruption through homologous recombination", Appl. Microbiol. Biotechnol., vol. 42, pp. 353-357 (1994).
C. Ohto et al., "Prenyl Alcohol Production by Expression of Exogenous Isopentenyl Diphosphate Isomerase and Farnesyl Diphosphate Synthase Genes in *Escherichia coli*", Biosci. Biotechnol. Biochem., vol. 73, No. 1, pp. 186-188 (2009).

\* cited by examiner

*Primary Examiner* — Ganapathirama Raghu
(74) *Attorney, Agent, or Firm* — Sunstein Kann Murphy & Timbers LLP (57) ABSTRACT

The present invention relates to a modified yeast strain which is prepared by introducing a vector that expresses HMG-CoA reductase (hydroxymethylglutaryl CoA reductase) and farnesyl pyrophosphate synthase, and a method for producing squalene using the same. More particularly, the present invention relates to *Saccharomyces cerevisiae* Y2805 modified yeast strain that is transformed with a vector including the HMG1 gene, and ispA or Erg20 gene, and a method for producing squalene with high efficiency by culturing the modified yeast strain.

10 Claims, 2 Drawing Sheets

```
                              SEQUENCE LISTING

<160> NUMBER OF SEQ ID NOS: 15

<210> SEQ ID NO 1
<211> LENGTH: 1578
<212> TYPE: DNA
<213> ORGANISM: Saccharomyces cerevisiae
<220> FEATURE:
<221> NAME/KEY: gene
<222> LOCATION: (1)..(1578)
<223> OTHER INFORMATION: HMG1

<400> SEQUENCE: 1
atggaccaat tggtgaaaac tgaagtcacc aagaagtctt ttactgctcc tgtacaaaag      60
gcttctacac cagttttaac caataaaaca gtcatttctg gatcgaaagt caaaagttta     120
tcatctgcgc aatcgagctc atcaggacct tcatcatcta gtgaggaaga tgattcccgc     180
gatattgaaa gcttggataa gaaaatacgt cctttagaag aattgaagc attattaagt      240 agtggaaata caaaacaatt gaagaacaaa gaggtcgctc ccttggttat tcacggtaag     300
ttacctttgt acgctttgga gaaaaaatta ggtgatacta cgagagcggt tgcggtacgt     360
aggaaggctc tttcaatttt ggcagaagct cctgtattag catctgatcg tttaccatat     420
aaaaattatg actacgaccg cgtatttggc gcttgttgtg aaaatgttat aggttacatg     480
cctttgcccg ttggtgttat aggccccttg gttatcgatg gtacatctta tcatatacca     540
atggcaacta cagagggttg tttggtagct tctgccatgc gtggctgtaa ggcaatcaat     600
gctggcggtg gtgcaacaac tgtttttaact aaggatggta tgacaagagg cccagtagtc    660
cgtttcccaa ctttgaaaag atctggtgcc tgtaagatat ggttagactc agaagaggga     720
caaaacgcaa ttaaaaaagc ttttaactct acatcaagat ttgcacgtct gcaacatatt     780
caaacttgtc tagcaggaga tttactcttc atgagattta gaacaactac tggtgacgca     840
atgggtatga atatgatttc taaaggtgtc gaatactcat taaagcaaat ggtagaagag     900
tatggctggg aagatatgga ggttgtctcc gtttctggta actactgtac cgacaaaaaa     960
ccagctgcca tcaactggat cgaaggtcgt ggtaagagtg tcgtcgcaga agctactatt    1020
cctggtgatg ttgtcagaaa agtgttaaaa agtgatgttt ccgcattggt tgagttgaac    1080
attgctaaga atttggttgg atctgcaatg gctgggtctg ttggtggatt taacgcacat    1140
gcagctaatt tagtgacagc tgttttcttg gcattaggac aagatcctgc acaaaatgtt    1200
gaaagttcca actgtataac attgatgaaa gaagtggacg tgatttgag aatttccgta    1260 tccatgccat ccatcgaagt aggtaccatc ggtggtggta ctgttctaga accacaaggt    1320
gccatgttgg acttattagg tgtaagaggc ccgcatgcta ccgctcctgg taccaacgca    1380
cgtcaattag caagaatagt tgcctgtgcc gtcttggcag gtgaattatc cttatgtgct    1440
gccctagcag ccggccattt ggttcaaagt catatgaccc acaacaggaa acctgctgaa    1500
ccaacaaaac ctaacaattt ggacgccact gatataaatc gtttgaaaga tgggtccgtc    1560
acctgcatta aatcctaa                                                  1578

<210> SEQ ID NO 2
<211> LENGTH: 2043
<212> TYPE: DNA
```

<213> ORGANISM: Artificial Sequence
<220> FEATURE:
<223> OTHER INFORMATION: MVAE gene

<400> SEQUENCE: 2

```
atgaagactg tcgttattat tgatgccttg agaactccta tcggtaaata taagggttct      60
ttatcacaag ttagtgccgt tgatcttggt acacacgtga caacgcaact attgaaaagg     120
cattcaacta tttctgaaga aattgatcaa gttatatttg gtaatgtttt acaagctgga     180
aatggacaaa accctgctag acaaattgct atcaacagtg gtctatcaca tgaaatacca     240
gcaatgaccg ttaatgaagt gtgtggtagt ggaatgaagg cagttatcct agctaagcaa     300
ctaattcaac taggagaagc agaggtactg attgctggcg gtattgaaaa tatgtcacaa     360
gcaccaaagt tacaaaggtt caattatgaa actgaatctt atgatgctcc cttctcctct     420
atgatgtacg atggtttaac tgatgctttc tcaggacaag caatgggttt gacagctgaa     480
aatgttgccg agaagtacca tgttactagg gaagaacaag atcagttttc cgtacatagt     540
caacttaaag cagctcaagc acaagctgaa ggtatctttg ccgatgaaat cgcacctctg     600
gaagtgtctg gtacacttgt ggaaaaggac gaaggcatta gaccaaattc atctgttgag     660
aaattaggta ccttgaagac tgttttaaa gaagatggta ctgtgactgc tggaaacgct     720
tccactatta tgatggtgc tagtgcttta attattgctt ctcaagaata tgctgaagcc     780
catggtttgc cttacttggc aatcatcaga gattcggttg aagtcggtat agatcctgct     840
tatatgggca tttcacctat taaagcaatt cagaagctgc tagccaggaa ccaactaacc     900
actgaagaaa ttgatcttta tgagatcaac gaggcatttg ccgccacatc tattgttgtt     960
caaagagaac ttgcattacc tgaagagaaa gtaaatatct atggtggcgg tatttctta    1020
ggtcatgcta tcggagctac tggtgctaga ttattgacga gcttgtctta ccaactgaat    1080
caaaagaga agaagtacgg tgtagcttca ttgtgtattg gtggtggcct tggactggcc    1140
atgctactag aaaggcctca acaaaagaaa aactccagat tctaccaaat gagtcctgaa    1200
gagaggttgg cttctctact gaacgaaggt caaatttctg ctgatactaa gaaagaattt    1260
gaaaacaccg ctttgtcttc acaaatagca aaccacatga tagaaaatca aatctcagaa    1320
acagaagtcc caatgggtgt tggtctacat ctaactgtgg atgaaaccga ttacttagtc    1380
cctatggcca cggaagaacc atcagtcatt gctgccttgt ctaatggtgc taagatcgca    1440
caaggtttta aaaccgtaaa tcaacaaaga ttgatgagag gtcaaattgt tttctacgac    1500
gtagctgatg ctgaatctct tatcgatgag ctgcaagtga gagagacgga aatttttcaa    1560
caagctgaat tatcctatcc atcgattgtc aaaaggggcg gcggacttag agatttgcag    1620
tatagagctt ttgatgaaag tttcgtctca gttgattttc tagtagacgt taaggatgcc    1680
atgggtgcaa acatcgttaa tgccatgctt gaaggtgtgg ccgaattatt cagagaatgg    1740
tttgctgaac aaaagatctt gtttagcatc ctatctaatt acgcaacaga aagcgtagtt    1800
acgatgaaaa cggcaattcc tgtatcaaga ttatccaaag gatctaatgg tagggaaatc    1860
gctgaaaaga ttgtcttagc atcaagatat gcttctctag atccatacag agccgtcaca    1920
cataacaaag gtattatgaa tggaatcgaa gccgttgttt tggcaacagg taatgatacc    1980
agggctgttt cagcctcttg tcatgccttt gcagtcaaag aaggcagata tcaaggacta    2040
tag                                                                  2043
```

<210> SEQ ID NO 3
<211> LENGTH: 900
<212> TYPE: DNA

```
<213> ORGANISM: Escherichia coli
<220> FEATURE:
<221> NAME/KEY: gene
<222> LOCATION: (1)..(900)
<223> OTHER INFORMATION: ispA

<400> SEQUENCE: 3
atggactttc cgcagcaact cgaagcctgc gttaagcagg ccaaccaggc gctgagccgt       60
tttatcgccc cactgcccct tcagaacact cccgtggtcg aaaccatgca gtatggcgca      120
ttattaggtg gtaagcgcct gcgacctttc ctggtttatg ccaccggtca tatgttcggc      180
gttagcacaa acacgctgga cgcacccgct gccgccgttg agtgtatcca cgcttactca      240
ttaattcatg atgatttacc ggcaatggat gatgacgatc tgcgtcgcgg tttgccaacc      300
tgccatgtga gtttggcga agcaaacgcg attctcgctg cgacgctttt acaaacgctg      360
gcgttctcga ttttaagcga tgccgatatg ccggaagtgt cggaccgcga cagaatttcg      420
atgatttctg aactggcgag cgccagtggt attgccggaa tgtgcggtgg tcaggcatta      480
gatttagacg cggaaggcaa acacgtacct ctggacgcgc ttgagcgtat tcatcgtcat      540
aaaaccggcg cattgattcg cgccgccgtt cgccttggtg cattaagcgc cggagataaa      600
ggacgtcgtg ctctgccggt actcgacaag tatgcagaga gcatcggcct tgccttccag      660
gttcaggatg acatcctgga tgtggtggga gatactgcaa cgttgggaaa acgccagggt      720
gccgaccagc aacttggtaa aagtaccctac cctgcacttc tgggtcttga gcaagcccgg      780
aagaaagccc gggatctgat cgacgatgcc cgtcagtcgc tgaaacaact ggctgaacag      840
tcactcgata cctcggcact ggaagcgcta gcggactaca tcatccagcg taataaataa      900

<210> SEQ ID NO 4
<211> LENGTH: 876
<212> TYPE: DNA
<213> ORGANISM: Abies grandis
<220> FEATURE:
<221> NAME/KEY: gene
<222> LOCATION: (1)..(876)
<223> OTHER INFORMATION: GPPS

<400> SEQUENCE: 4
atgtacatgg attccaaggc aatgacagtg aatgaggcgt tgaataaggc tatcccactt       60
cgttatcccc agaaaatata tgaatccatg aggtattctc ttctggcagg agggaaacga      120
gttcgtcctg ttctgtgcat tgcagcatgt gagcttgttg gaggaaccga ggagcttgcg      180
attccaactg cctgtgcaat cgaaatgatc cacacaatgt cttttgatgca tgatgacttg      240 ccttgcatag acaatgatga tttacggcga gggaaaccta caaaccataa gatcttcggg      300
gaagatactc tgttactgc agggaatgcg cttcattctt acgcctttga gcatattgca      360
gtttccacaa gcaaaactgt gggggctgat aggattttga ggatggtatc tgaactgggt      420
agagcaacag gctctgaagg ggttatggt ggccagatgg tcgatattgc cagcgaaggg      480
gatccttcta ttgaccttca gactctggaa tggattcata ttcacaagac tgcaatgctc      540
ttggagtgct cggttgtgtg tggggcgatc atcgtggtg cttcggagat tgtgatcgag      600
agagctcgaa ggtatgcccg ttcgtgggg cttctttttc aggttgtgga tgacatactc      660
gatgtcacga atcatcaga cgaactgggc aagactgcag gaaaggattt tgattagtgat      720 aaggcaactt atccaaagct catgggtttg gagaaagcaa aggagttttc tgatgaattg      780
ttgaacagag ctaagggaga gttatcttgc ttcgatccag tgaaggcagc acctctgttg      840
ggtcttgcag attacgtggc attcagacaa aattaa                                876
```

<210> SEQ ID NO 5
<211> LENGTH: 1059
<212> TYPE: DNA
<213> ORGANISM: Saccharomyces cerevisiae
<220> FEATURE:
<221> NAME/KEY: gene
<222> LOCATION: (1)..(1059)
<223> OTHER INFORMATION: Erg20

<400> SEQUENCE: 5

```
atggcttcag aaaagaaat taggagagag agattcttga acgttttccc taaattagta      60
gaggaattga acgcatcgct tttggcttac ggtatgccta aggaagcatg tgactggtat     120
gcccactcat tgaactacaa cactccaggc ggtaagctaa atagaggttt gtccgttgtg     180
gacacgtatg ctattctctc caacaagacc gttgaacaat tggggcaaga agaatacgaa     240
aaggttgcca ttctaggttg gtgcattgag ttgttgcagg cttacttctt ggtcgccgat     300
gatatgatgg acaagtccat taccagaaga ggccaaccat gttggtacaa ggttcctgaa     360
gttggggaaa ttgccatcaa tgacgcattc atgttagagg ctgctatcta caagcttttg     420
aaatctcact tcagaaacga aaatactac atagatatca ccgaattgtt ccatgaggtc     480
accttccaaa ccgaattggg ccaattgatg gacttaatca ctgcacctga agacaaagtc     540
gacttgagta agttctcct aaagaagcac tccttcatag ttactttcaa gactgcttac     600
tattctttct acttgcctgt cgcattggcc atgtacgttg ccggtatcac ggatgaaaag     660
gatttgaaac aagccagaga tgtcttgatt ccattgggtg aatacttcca aattcaagat     720
gactacttag actgcttcgg tacccccagaa cagatcggta agatcggtac agatatccaa     780
gataacaaat gttcttgggt aatcaacaag gcattggaac ttgcttccgc agaacaaaga     840
aagactttag acgaaaatta cggtaagaag gactcagtcg cagaagccaa atgcaaaaag     900
attttcaatg acttgaaaat tgaacagcta taccacgaat atgaagagtc tattgccaag     960
gatttgaagg ccaaaatttc tcaggtcgat gagtctcgtg gcttcaaagc tgatgtctta    1020
actgcgttct tgaacaaagt ttacaagaga agcaaatag                           1059
```

<210> SEQ ID NO 6
<211> LENGTH: 28
<212> TYPE: DNA
<213> ORGANISM: Artificial Sequence
<220> FEATURE:
<223> OTHER INFORMATION: Forward primer for HMG1

<400> SEQUENCE: 6

```
aaaagaattc atggaccaat tggtgaaa                                          28
```

<210> SEQ ID NO 7
<211> LENGTH: 28
<212> TYPE: DNA
<213> ORGANISM: Artificial Sequence
<220> FEATURE:
<223> OTHER INFORMATION: Reverse primer for HMG1

<400> SEQUENCE: 7

```
aaaagtcgac ttaggattta atgcaggt                                          28
```

<210> SEQ ID NO 8
<211> LENGTH: 37
<212> TYPE: DNA
<213> ORGANISM: Artificial Sequence
<220> FEATURE:
<223> OTHER INFORMATION: Forward primer for ispA

```
<400> SEQUENCE: 8
atggaattca aaatggact ttccgcagca actcgaa                                37

<210> SEQ ID NO 9
<211> LENGTH: 38
<212> TYPE: DNA
<213> ORGANISM: Artificial Sequence
<220> FEATURE:
<223> OTHER INFORMATION: Reverse primer for ispA

<400> SEQUENCE: 9
cggactacat catccagcgt aataaataag tcgacctc                              38

<210> SEQ ID NO 10
<211> LENGTH: 37
<212> TYPE: DNA
<213> ORGANISM: Artificial Sequence
<220> FEATURE:
<223> OTHER INFORMATION: Forward primer for GPPS

<400> SEQUENCE: 10
atggaattca aaatgtaca tggattccaa ggcaatg                                37

<210> SEQ ID NO 11
<211> LENGTH: 36
<212> TYPE: DNA
<213> ORGANISM: Artificial Sequence
<220> FEATURE:
<223> OTHER INFORMATION: Reverse primer for GPPS

<400> SEQUENCE: 11
gaggtcgact taattttgtc tgaatgccac gtaatc                                36

<210> SEQ ID NO 12
<211> LENGTH: 43
<212> TYPE: DNA
<213> ORGANISM: Artificial Sequence
<220> FEATURE:
<223> OTHER INFORMATION: Forward primer for Erg20

<400> SEQUENCE: 12
atggaattca aaatggctt cagaaaaaga aattaggaga gag                         43

<210> SEQ ID NO 13
<211> LENGTH: 40
<212> TYPE: DNA
<213> ORGANISM: Artificial Sequence
<220> FEATURE:
<223> OTHER INFORMATION: Reverse primer for Erg20

<400> SEQUENCE: 13
cttgaacaaa gtttacaaga gaagcaaata actcgagctc                            40

<210> SEQ ID NO 14
<211> LENGTH: 24
<212> TYPE: DNA
<213> ORGANISM: Artificial Sequence
<220> FEATURE:
<223> OTHER INFORMATION: ScADH1-F primer

<400> SEQUENCE: 14
gagctctgta gccctagact tgat                                             24

<210> SEQ ID NO 15
<211> LENGTH: 24
<212> TYPE: DNA
```

```
<213> ORGANISM: Artificial Sequence
<220> FEATURE:
<223> OTHER INFORMATION: ScADH1-R primer

<400> SEQUENCE: 15
gaattctgta tatgagatag ttga                                          24
```

MODIFIED YEAST STRAIN AND A METHOD FOR PRODUCING SQUALENE USING THE SAME

CROSS-REFERENCE TO RELATED APPLICATION

This application is a Continuation-in-Part of PCT international application Ser. No. PCT/KR2010/007621, filed Nov. 1, 2010, designating the United States, which claims the benefit of Korean Application No. 10-2009-0104505, filed on Oct. 30, 2009. The entire contents of the aforementioned patent applications are incorporated herein by this reference.

SEQUENCE LISTING

The instant application contains a Sequence Listing which has been submitted in ASCII format via EFS-Web and is hereby incorporated by reference in its entirety. Said ASCII copy, created on Aug. 30, 2012, is named 90722_CIP_311624_ST25.txt and is 11,602 bytes in size.

TECHNICAL FIELD

The present invention relates to a modified yeast strain which is prepared by introducing a vector that expresses HMG-CoA reductase (hydroxymethylglutaryl CoA reductase) and farnesyl pyrophosphate synthase, and a method for producing squalene using the same. More particularly, the present invention relates to Saccharomyces cerevisiae Y2805 modified yeast strain that is transformed with a vector including the HMG1 gene, and ispA or Erg20 gene, and a method for producing squalene with high efficiency by culturing the modified yeast strain.

BACKGROUND ART

Squalene (2,6,10,15,19,23-hexamethyltetracosa-2,6,10,14,18,22-hexaene), a dehydro-triterpenic hydrocarbon ($C_{30}H_{50}$) with six double bonds as shown in Chemical Formula 1, is one of the terpenoid compounds forming various chemicals and a precursor of all steroids in plants and animals.

It has been revealed that squalene can effectively inhibit chemically induced skin, lung, and colon tumorigenesis in rodents (Aioi A et al., 1995, Int. J. Pharm., 113, 159-164), and supplementation of squalene-containing diets can activate nonspecific immune functions, affect the absorption efficiency of cholesterol, and lower LDL (low-density lipoprotein) and triglyceride levels. Squalene, the main component of skin surface polyunsaturated lipids, shows antioxidant and moisturizing effects on skin, and thus can be used as a raw material for cosmetics. Recently, it has been also approved for use in drug delivery, in particular, as a vaccine adjuvant (Tritto E. et al., 2009, Vaccine, 27, 3331-3334).

Up to the present, the major commercial source of squalene has been liver oils of deep-sea sharks and certain plant seed oils. However, the continuous supply of the liver oils of deep-sea sharks is in doubt because of environmental pollutants such as heavy metals, concerns over the preservation of marine wildlife, and the supply of the plant seed oils (e.g., olive oil 7 mg/g, amaranth oil 0-5.64 mg/g) is also in doubt because of the effects of seasonal change and geographical variations on the crop production.

Therefore, many studies have been made on the methods for producing squalene, including on the use of squalene-producing yeasts such as Pseudozyma (Chang M H et al., 2008, Appl. Microbiol. Biotechnol., 78, 963-972), Candida famata (JP 07,289,272), and Torulaspora delbrueckii (Bhattacharjee P. et al., 2001, World J. Microbiol. Biotechnol., 17, 811-816), the use of Euglena (JP 07,115,981), and the use of microalgae such as Botryococcus braunii (Okada S. et al., 2000, Arch. Biochem. Biophys., 373, 307-317) and thraustochytrids (Li Q et al., 2009, J. Agric. Food Chem., 57, 4267-4272).

However, these methods do not show sufficient productivity required for commercialization, because of the long period of time required for cell cultivation, low cell productivity, and low squalene yield per cell. Thus, studies have focused on metabolic engineering technologies for high production of squalene.

Saccharomyces cerevisiae has been frequently used as a host cell in metabolic engineering. This yeast has been known to accumulate ergosterol to 1% per dry cell weight on average, and up to 4.6% per dry cell weight depending on the strain or culture conditions (Arnezeder C. et al., 1990, Biotechnol. Lett., 12, 277-282), and thus can be used for the production of squalene that is an intermediate of the ergosterol biosynthetic pathway. However, the accumulation of squalene is very low under normal growth conditions, because it is an intermediate of the ergosterol biosynthetic pathway. That is, squalene productivity of Saccharomyces cerevisiae and Torulaspora delbrueckii is at most 41.16 and 237.25 μg per gram of wet cell, respectively (Bhattacharjee P. et al., 2001, World J. Microbiol. Biotechnol., 17, 811-816), and another recent study revealed that Saccharomyces cerevisiae (BY4741 and EGY48 stains) showed low productivity of approximately 3 mg/l and 3.1 mg/l under semianaerobic conditions (Mantzouridou F. et al., J. Agric. Food Chem. 57, 6189-6198 (2009).

Figures 1, 2:
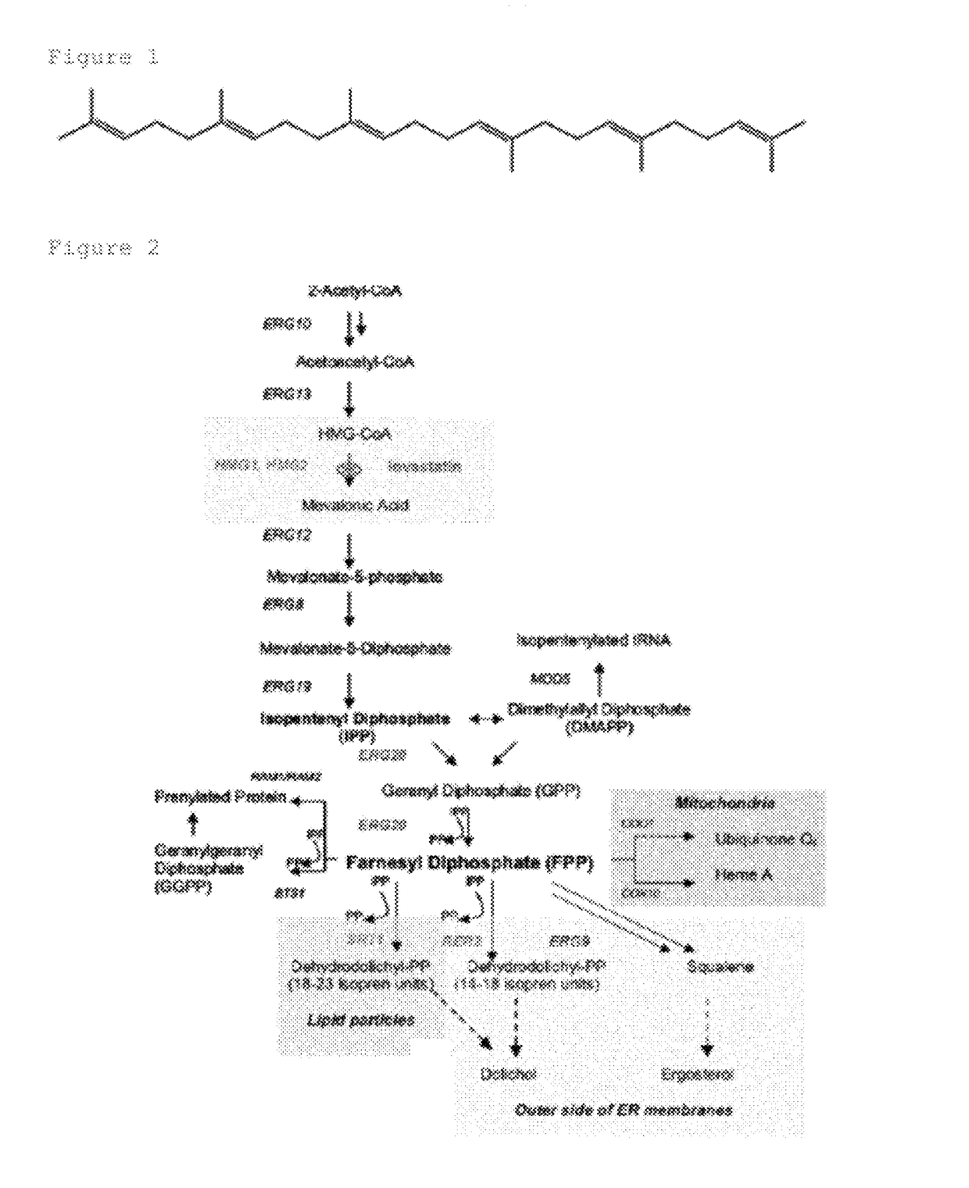
FIG. 1 is a schematic diagram showing the chemical structure of squalene.
FIG. 2 is a schematic diagram showing the mevalonate biosynthetic pathway of the yeast *Saccharomyces cerevisiae*.

Therefore, metabolic engineering technologies are needed for high accumulation of squalene in yeast. Ergosterol and squalene are isoprenoid or terpenoid compounds. Isoprenoid biosynthetic pathways are largely classified into mevalonate and non-mevalonate pathways, and the mevalonate pathway is ubiquitous in eukaryotes. Because the yeast Saccharomyces cerevisiae is a eukaryotic cell, the mevalonate pathway is ubiquitous therein. The ergosterol biosynthetic pathway is as shown in FIG. 2.

In the mevalonate biosynthetic pathway, the HMG (hydroxymethylglutaryl CoA reductase) step of producing mevalonate is known to be the most important rate-determining step. The step is under various regulatory mechanisms, and overexpression of the HMG gene leads to enhancement of the isoprenoid biosynthetic metabolism. Thus, there have been many attempts to overexpress the HMG gene for excessive production of various isoprenoids (farnesol), geranylgeraniol, and amorphadiene in Saccharomyces cerevisiae (WO2008039499; U.S. Patent No. 20040235088; U.S. Patent No. 20030092144; Tokuhiro K. et al., 2009, Appl. Environ. Microbiol., 75, 5536-5543; Ohto C. et al., 2009, Appl. Micorbiol. Biotechnol., 82, 837-845). It has been known that this method is also useful for squalene production, and overexpression of the HMG1 gene accumulates squalene up to 0.9% per dry yeast cell weight (Polakowski T. et al., 1998, Appl. Microbiol. Biotechnol., 49, 66-71), or 2% per dry yeast cell weight (Donald K A et al., 1997, Appl. Environ. Microbiol., 63, 3341-3344). In addition, a recent study has reported that squalene productivity of 106-192 mg/l (2.3-4.1 mg/g DCW) can be achieved by overexpressing the HMG1 gene in Saccharomyces cerevisiae YPH499 using the GAPDH promoter (Tokuhiro K. et al., Appl. Environ. Microbiol. 75, 5536-5543 (2009)).

Meanwhile, another method for squalene accumulation is to disrupt a gene required for the conversion of squalene to ergosterol by homologous recombination, resulting in accumulation of approximately 5 mg/g of squalene (Kamimura N. et al., 1994, Appl. Microbiol. Biotechnol., 42, 353-357). Ohto et al. recently examined the overexpression effects of various genes involved in the mevalonate pathway (ERG10, HMG synthase, HMG1, ERG12, ERG8, ERG19, IDI1, idi, ERG20, ispA) on the productivities of prenyl alcohols such as farnesol, nerolidol, and geranylgeraniol, and squalene in *Saccharomyces cerevisiae* (Ohto C. et al., 2009, Appl. Micorbiol. Biotechnol., 82, 837-845), showing that HMG1 was the most effective. However, the ispA (*E. coli*-derived farnesyl pyrophosphate synthase) gene, which is known to increase the productivity of prenyl alcohols up to 5-6 fold in *E. coli*, did not show any effects on the improvement of productivity when overexpressed in *Saccharomyces cerevisiae* (Ohto C. et al., Biosci. Biotechnol. Biochem. 73, 186-188 (2009)). The Erg20 gene, which is the yeast-derived farnesyl pyrophosphate synthase gene, also showed poor effects when overexpressed. The present inventors supposed that the isoprenoid biosynthetic pathway of the eukaryotic yeast is the mevalonate pathway, unlike the non-mevalonate pathway in the prokaryotic *E. coli*, and an accumulation of farnesyl pyrophosphate as the product of ispA or Erg20 enzyme in the mevalonate pathway inhibits HMG1 gene expression or its enzymatic activity as a regulatory step in the overall isoprenoid biosynthetic pathway.

Accordingly, the present inventors have made many efforts to develop a modified yeast strain for the production of squalene with high efficiency. As a result, they found that the GAL10 or ADH1 promoter can be used as a promoter for the HMG1 gene expression instead of its own promoter to overcome the inhibition of the HMG1 gene expression by the products of isoprenoid biosynthetic pathways and to develop a method of co-overexpressing the farnesyl pyrophosphate synthase gene such as ispA and Erg20, and the HMG1 gene, and the developed modified yeast strain, *Saccharomyces cerevisiae* Y2805, shows higher productivity by several- to several-tens-fold, compared to the YPH499 strain known to produce squalene with high efficiency, thereby completing the present invention.

DISCLOSURE

Technical Problem

An object of the present invention is to provide a modified yeast strain that is prepared by introduction of a vector expressing HMG-CoA reductase and farnesyl pyrophosphate synthase.

Another object of the present invention is to provide a method for producing squalene by culturing the modified yeast strain.

Best Mode

In one aspect to achieve the above objects, the present invention relates to a modified yeast strain that is prepared by introduction of a vector expressing HMG-CoA reductase (hydroxymethylglutaryl CoA reductase) and farnesyl pyrophosphate synthase.

The modified yeast strain is transformed with a vector expressing HMG-CoA reductase (hydroxymethylglutaryl CoA reductase) and farnesyl pyrophosphate synthase, so that the genes are overexpressed to accumulate an excessive amount of squalene in the yeast.

As used herein, the term "HMG-CoA reductase" refers to an enzyme involved in the metabolic pathway that produces cholesterol and other isoprenoids. In particular, it is known as an important rate-determining enzyme for the mevalonate pathway.

The enzyme is an anchored protein embedded in the membrane of ER (endoplasmic reticulum), and has 7 transmembrane domains. For excessive production of squalene, there have been attempts to regulate the HMG1 gene expression. However, a significant increase in the squalene production could not be achieved due to the complicated mechanism of the related pathway or it was difficult to produce a strain showing a constant expression level for industrialization. In addition, a modified yeast strain producing squalene with high stability and efficiency has not been developed yet.

In one preferred embodiment, any gene may be used without limitation, as long as it is able to show HMG-CoA reductase activity in yeast, and preferable is the HMG1 gene encoding the HMG-CoA reductase. In the preferred Example of the present invention, squalene could be produced with high efficiency from the modified yeast strain that was transformed with the HMG1 gene derived from *Saccharomyces cerevisiae* as the HMG-CoA reductase.

The HMG1 gene can be divided into a transmembrane domain and a catalytic domain according to the functions of the regions encoded by the gene, and in the present invention, an entire, a part or a fragment of the gene expressing the catalytic domain may be used as an insertable gene without limitation. More preferably, the HMG1 gene of the present invention is a gene modified to express the catalytic domain only without the transmembrane domain, and the modification prevents the feedback regulation of the intermediates in the ergosterol biosynthetic pathway, thereby improving the content of squalene.

As used herein, the term "farnesyl pyrophosphate synthase" refers to an enzyme catalyzing the synthesis of farnesyl pyrophosphate from isopentenyl pyrophosphate and dimethylallyl pyrophosphate. In particular, farnesyl pyrophosphate synthase is a key enzyme in the ergosterol biosynthesis pathway that supplies C15 precursors for the structurally diverse classes of essential metabolites, and is an enzyme producing farnesyl pyrophosphate as the immediate precursor of squalene.

Any gene encoding the farnesyl pyrophosphate synthase may be used without limitation, as long as it is able to show the enzymatic activity in yeast. Examples of the farnesyl pyrophosphate synthase gene useful in the present invention may include ispA gene and Erg20 gene, but are not limited thereto. Moreover, the origin of the ispA gene or the Erg20 gene is not limited, as long as the corresponding gene has its intrinsic activity in yeast. Preferably, the ispA gene may be derived from *E. coli*, and the Erg20 gene may be derived from *Saccharomyces cerevisiae*.

As used herein, the term "ergosterol biosynthetic pathway" or "isoprenoid biosynthetic pathway" can be interchangeably used, and the biosynthetic pathway produces squalene as an intermediate product. The modified yeast strain of the present invention is able to produce squalene with high efficiency by concurrent overexpression of HMG-CoA reductase and farnesyl pyrophosphate synthase in the biosynthetic pathway.

As used herein, the term "squalene" belongs to the group of isoprenoids or terpenoids, and is a polyunsaturated lipid ($C_{30}H_{50}$) with six double bonds, as shown in Chemical Formula 1.

Chemical Formula 1

As used herein, the term "vector", which describes an expression vector capable of expressing a target protein in a suitable host cell, refers to a genetic construct that includes essential regulatory elements to which a gene insert is operably linked in such a manner as to be expressed in a host cell.

The operable linkage to a recombinant vector may be prepared using a genetic recombinant technique well known in the art, and site-specific DNA cleavage and ligation may be carried out using enzymes generally known in the art.

The vector of the present invention may include a signal sequence or a leader sequence for targeting membranes or secretion as well as expression regulatory elements, such as a promoter, an operator, an initiation codon, a stop codon, a polyadenylation signal and an enhancer, and can be constructed in various forms depending on the purpose thereof. The promoter of the vector may be constitutive or inducible. In addition, expression vectors include a selectable marker that allows the selection of host cells containing the vector, and replicable expression vectors include a replication origin. The vector may be self-replicable, or may be integrated into the host DNA. The vector includes a plasmid vector, a cosmid vector, a viral vector or the like, and any vector known in the art may be used without limitation, as long as it is able to express the desired gene in the yeast host cell.

As used herein, the term "operably linked" refers to the linkage of nucleic acid fragments in such a functional relationship that when expressed, each of them can operate without functional problems, whereas, when one neucleic acid fragment is connected to the other, its function and expression may be affected by the other. For instance, the term refers to a functional linkage between a nucleic acid sequence coding for the desired protein and a nucleic acid expression control sequence in such a manner as to allow general functions. In addition, the expression cassette of the present invention may further include any transcription initiation regulating sequence and transcription termination regulating sequence for transcription regulation. The operable linkage may be prepared using a genetic recombinant technique that is well known in the art, and site-specific DNA cleavage and ligation may be carried out using enzymes that are generally known in the art.

As used herein, the term "introduction" refers to the insertion of foreign DNA into a cell by transformation or transduction. The transformation may be performed by various methods known in the art, such as a $CaCl_2$ precipitation, a Hanahan method that is an improved $CaCl_2$ method by using DMSO (dimethyl sulfoxide) as a reducing material, electroporation, calcium phosphate precipitation, protoplast fusion, agitation using silicon carbide fiber, *Agrobacterium*-mediated transformation, PEG-, dextran sulfate-, lipofectamine-, and desiccation/inhibition-mediated transformation. The transduction refers to the delivery of a gene to a cell using a virus or viral vector particle by means of infection.

In one preferred embodiment, the vector expressing the enzyme is introduced to improve its intracellular enzymatic activity, which can be achieved by overexpression of the gene. The overexpression of the desired gene can be enhanced by modification of the nucleic acid sequences of the promoter region and 5' UTR region of the gene, leading to an enhancement of protein expression. The expression can be enhanced by an additional introduction of the desired gene into the chromosome, and the protein expression level can be enhanced by transformation of a strain with a vector having the desired gene with a self promoter or a different enhanced promoter. It can be also achieved by introducing mutation in ORF (open reading frame) region of the desired gene. According to determination of the overexpression, activity or concentration of the corresponding protein was found to increase by at least 10%, 25%, 50%, 75%, 100%, 150%, 200%, 300%, 400% or 500%, and up to 1000% or 2000%, based on the wild-type protein or the activity or concentration of the initial microorganism strain. Preferably, its intracellular enzymatic activity can be improved by an introduction of a vector expressing the enzyme.

In one preferred embodiment, the promoter operably linked to the gene encoding HMG-CoA reductase and farnesyl pyrophosphate synthase is preferably a foreign promoter in order to prevent reduction of HMG-CoA reductase activity. In order to achieve this object, the GAL10 promoter or ADH1 promoter may be operably linked to the upstream of the gene of the present invention.

Figure 3:
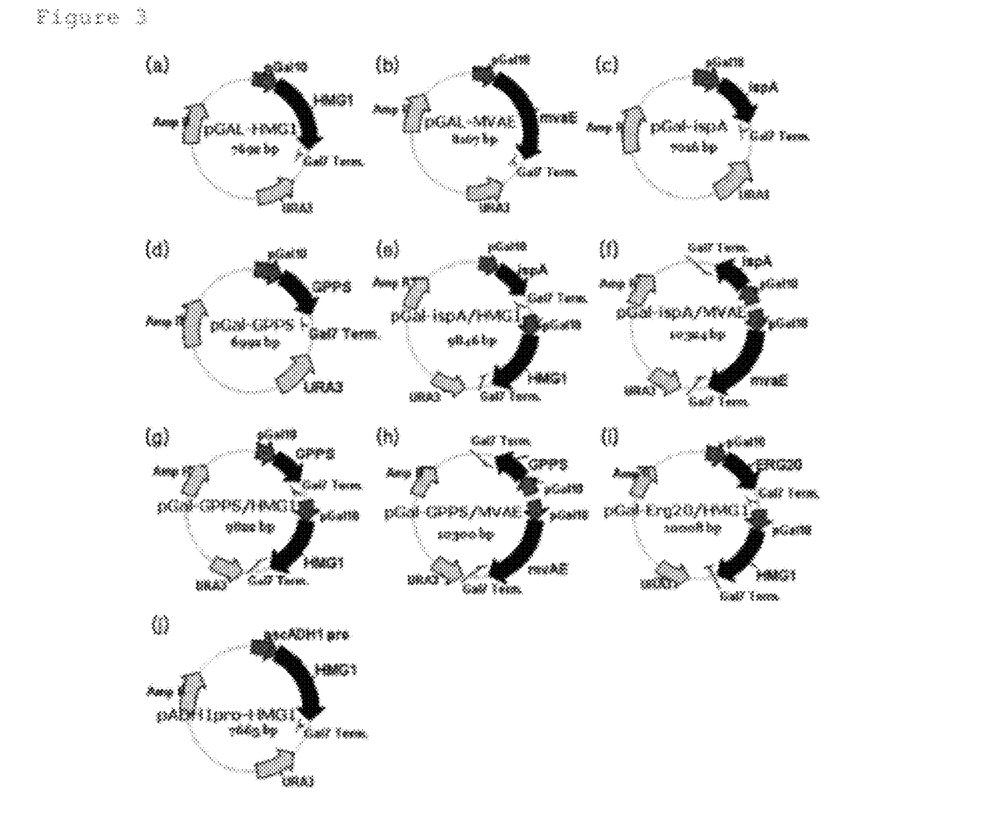
FIG. 3 is a schematic diagram showing vectors for the squalene biosynthesis.

In one preferred embodiment, the vector expressing HMG-CoA reductase and farnesyl pyrophosphate synthase may be a pGal-ispA/HMG1 vector having a cleavage map of FIG. 3(e), in which the vector includes an expression cassette having the GAL10 promoter operably linked to the HMG1 gene and the GAL10 promoter operably linked to the ispA gene, or a pGal-Erg20/HMG1 vector having a cleavage map of FIG. 3(i), in which the vector includes an expression cassette having the GAL10 promoter operably linked to the HMG1 gene and the GAL10 promoter operably linked to the Erg20 gene.

In one preferred embodiment, the modified yeast strain may be any yeast without limitation, as long as it is able to produce squalene with high efficiency by introduction of the vector expressing HMG-CoA reductase and farnesyl pyrophosphate synthase. Examples thereof may include the genus *Saccharomyces cerevisiae*, preferably *Saccharomyces cerevisiae*, and more preferably *Saccharomyces cerevisiae* Y2805.

In one preferred embodiment, the modified yeast strain may be a modified yeast strain designated as *Saccharomyces cerevisiae* Y2805/pGal-ispA/HMG1 which was prepared by introduction of the pGal-ispA/HMG1 vector (FIG. 3(e)) into *Saccharomyces cerevisiae* Y2805, and has been deposited at the Genetic Resources Center, Korea Research Institute of Bioscience and Biotechnology (111 Gwahangno, Yuseong-gu, Daejeon) on Oct. 19, 2009 under the Accession number KCTC 11577BP, or a modified yeast strain designated as *Saccharomyces cerevisiae* Y2805/pGal-Erg20/HMG1 which was prepared by introduction of the pGal-Erg20/HMG1 vector (FIG. 3(i)) into *Saccharomyces cerevisiae* Y2805, and has been deposited at the Genetic Resources Center, Korea Research Institute of Bioscience and Biotechnology (111 Gwahangno, Yuseong-gu, Daejeon) on Oct. 19, 2009 under the Accession number KCTC 11578BP.

In one preferred Example, the present inventors constructed a total of 10 vectors, (FIG. 3) pGal-ispA, pGal-HMG1, pADH-HMG1, pGal-MVAE, pGal-GPPS, pGal-ispA/HMG1, pGal-ispA/MVAE, pGal-GPPS/HMG1, pGal-GPPS/MVAE and pGal-Erg20/HMG1, prepared by cloning into yeast expression vectors the various genes of the isoprenoid biosynthetic pathway that are expected to be involved in squalene synthesis. They were introduced each vector into *Saccharomyces cerevisiae* Y2805. Then, they were cultured the modified yeast strains, and analyzed the amounts of squalene accumulated in the modified yeast strains by gas chromatography. As a result, the modified yeast strains transformed with pGal-ispA/HMG1 and pGal-Erg20/HMG1 were found to produce 1.246 g/l and 0.886 g/l of squalene, respectively. These production amounts are higher than 0.001~0.114 g/l of squalene produced by the strains transformed with other genes (Table 4), indicating that a remarkably high level of squalene can be produced by co-overexpression of HMG-CoA reductase and farnesyl pyrophosphate synthase by the modified yeast strain of the present invention.

In addition, the co-overexpression effects of HMG1 gene and ispA gene on squalene productivity were examined according to yeast strains. As a result, Y2805 was found to produce 1.004 g/l of squalene, which is several tens-fold higher than those of the ATCC 201741, ATCC 201238, and ATCC 200589 recently known as the strains having high isoprenoid productivity (Table 5).

In another aspect, the present invention relates to a method for producing squalene by culturing the modified yeast strain.

The modified yeast strain overexpressing BMG-CoA reductase and farnesyl pyrophosphate synthase may be cultured according to the various yeast cultivation methods known in the art. For example, after initial cultivation using YNB media, YPGlu1% Gal1% media may be used for the main cultivation, but the cultivation method of the modified yeast strain is not limited thereto. In addition, the accumulated squalene may be obtained by typical isolation and extraction methods. In the preferred Example of the present invention, after disruption of the cells, pentane was added, and squalene dissolved in the pentane layer was isolated.

Advantageous Effects

The modified yeast strain of the present invention is used to overcome many limitations of the current sources of squalene and to produce squalene as a raw material for cosmetics or medicine with high efficiency. It is also expected to lower the high price of squalene due to short supply and high production costs.

MODE FOR INVENTION

Hereinafter, the present invention will be described in more detail with reference to Examples. However, these Examples are for illustrative purposes only, and the invention is not intended to be limited thereby.

Example 1

Construction of Squalene-Producing Strain

In order to produce squalene with high efficiency in the yeast strain *Saccharomyces cerevisiae*, overexpression of the genes responsible for isoprenoid biosynthetic pathway including HMG CoA reductase is required. Thus, the various genes of the isoprenoid biosynthetic pathway, expected to be involved in squalene synthesis, were cloned into yeast expression vectors (FIG. 3).

Firstly, the *Enterococcus faecalis*-derived bifunctional enzyme, and the MVAE gene having both acetyl-CoA acetyl transferase/hydroxymethyl glutaryl (HMG)-CoA reductase activities were artificially synthesized by GenScript Corp with a yeast codon bias (SEQ ID NO. 2), and the 5'- and 3'-ends thereof were constructed to have the EcoRI and SalI recognition sites. The gene was cleaved with EcoRI and SalI, and inserted into an expression vector YEGα-HIR525 that was treated with the same restriction enzymes. The expression vector is a vector having the GAL10 promoter, and the target gene was cloned between the EcoRI site downstream of the promoter and the SalI site upstream of the GAL7 terminator.

From hydroxymethyl glutaryl CoA reductase biosynthesizing mevalonate from HMG CoA, the N-terminal transmembrane domain (597 aa) known to cause enzyme degradation by a control mechanism was removed to prepare the *Saccharomyces cerevisiae*-derived HMG1 gene having a catalytic domain only (SEQ ID NO. 1). GPPS (Geranyl pyrophosphate synthase) gene (SEQ ID NO. 4) was acquired from an *Abies grandis* plant, and the *E. coli* derived ispA gene (SEQ ID NO. 3) and the *Saccharomyces cerevisiae*-derived Erg20 gene (SEQ ID NO. 5) were used as FPP (farnesyl pyrophosphate) synthase gene. Each PCR products obtained by using the genes and primers of the following Table 1 were restricted with EcoRI and SalI, and inserted into the expression vector YEGα-HIR525 treated with the same restriction enzymes.

TABLE 1

<Primer sequences and Restriction enzymes used in gene cloning>

| Gene | Primer sequence | SEQ ID NO. | Restriction enzyme |
|---|---|---|---|
| HMG1 F | 5'-AAAAGAATTCATGGACCAATTGGTGAAA-3' | 6 | EcoRISalI |
| R | 5'-AAAAGTCGACTTAGGATTTAATGCAGGT-3' | 7 | |
| IspA F | 5'-ATGGAATTCAAAAATGGACTTTCCGCAGCAACTCGAA-3' | 8 | EcoRISalI |
| R | 5'-CGGACTACATCATCCAGCGTAATAAATAAGTCGACCTC-3' | 9 | |

TABLE 1-continued

<Primer sequences and Restriction enzymes used in gene cloning>

| Gene | Primer sequence | SEQ ID NO. | Restriction enzyme |
|---|---|---|---|
| GPPS | F 5'-ATGGAATTCAAAAATGTACATGGATTCCAAGGCAATG-3' | 10 | EcoRISalI |
|  | R R 5'-GAGGTCGACTTAATTTTGTCTGAATGCCACGTAATC-3' | 11 |  |
| Erg20 | F 5'-ATGGAATTCAAAAATGGCTTCAGAAAAAGAAATTAGGAGAGAG-3' | 12 | EcoRIXhoI |
|  | R 5'-CTTGAACAAAGTTTACAAGAGAAGCAAATAACTCGAGCTC-3' | 13 |  |

To construct a co-expression vector for efficient squalene production, the ispA, Erg20 and GPPS genes were co-expressed with the HMG1 and MVAE genes.

The Saccharomyces-derived ADH1 promoter was used as the ADH1 promoter, and PCR amplification was performed using a primer set of ScADH1-F (5'-GAGCTCTGTAGC-CCTAGACTTGAT-3', SEQ ID NO. 14) and ScADH1-R (5'-GAATTCTGTATATGAGATAGTTGA-3', SEQ ID NO. 15) (restriction enzyme recognition sites are marked in bold italics) and the genomic DNA of Saccharomyces cerevisiae Y2805 strain as a template. The PCR product was subcloned into a pGEM-T easy vector, and its nucleic acid sequence was examined, and then treated with restriction enzymes, SacI and EcoRI. The GAL10 promoter of the YEGα-HIR525 vector was replaced with the gene including promoter region.

The 10 total vectors (FIG. 3), pGal-ispA, pGal-HMG1, pADH-HMG1, pGal-MVAE, pGal-GPPS, pGal-ispA/HMG1, pGal-ispA/MVAE, pGal-GPPS/HMG1, pGal-GPPS/MVAE and pGal-Erg20/HMG1, were each individually introduced into Saccharomyces cerevisiae Y2805. The Saccharomyces cerevisiae Y2805 was acquired from NIH (USA) (Sohn J H et al., J Microbiol. Biotechnol. 1, 266-273 (1991); Choi E S et al., Appl. Microbiol. Biotechnol 42, 587-594 (1994)).

The strain prepared by introduction of the pGal-ispA/HMG1 vector (FIG. 3(e)) into Saccharomyces cerevisiae Y2805 was designated as Saccharomyces cerevisiae Y2805/pGal-ispA/HMG1, and deposited at the Genetic Resources Center, Korea Research Institute of Bioscience and Biotechnology (111 Gwahangno, Yuseong-gu, Daejeon) on Oct. 19, 2009 under the Accession number KCTC 11577BP. In addition, the strain prepared by the introduction of the pGal-Erg20/HMG1 vector (FIG. 3(i)) into Saccharomyces cerevisiae Y2805 was designated as Saccharomyces cerevisiae Y2805/pGal-Erg20/HMG1, and deposited at the Genetic Resources Center, Korea Research Institute of Bioscience and Biotechnology (111 Gwahangno, Yuseong-gu, Daejeon) on Oct. 19, 2009 under the Accession number KCTC 11578BP.

Example 2

Strain Culture and Squalene Analysis

The cultivation was divided into initial cultivation and main cultivation. In the initial cultivation, YNB media was used. The YNB media was supplemented with 0.67% yeast nitrogen base W/O amino acids, 0.2% casamino Acid, and 2% glucose. A single colony was inoculated in 2 ml of YNB media, and initial cultivation was performed at 30° C., 180 rpm, followed by main cultivation. The main cultivation was performed using YPGlu1% Gal1% media (2% peptone, 1% yeast extract, 1% glucose, 1% galactose). Each 25 ml of YPGlu1% Gal1% media was put in a 250 ml baffled flask. The cultured strain was inoculated to show OD600 of 0.1, and cultured at 30° C. with shaking (180 rpm). After 72 hours, the produced squalene content in the strain was measured by GC (gas chromatography).

The squalene was analyzed as follows: 1 ml of culture broth was taken and centrifuged at 13,000 rpm for 1 minute to collect the cells. The cells were resuspended in 600 μl of 50 mM Tric-Cl (pH 7.5) and glass beads for 10 minutes. Next, 400 μl of pentane was added thereto, and squalene was dissolved in a pentane layer by sufficient resuspension. Then, centrifugation was performed at 13,000 rpm for 5 minutes, and quantification for the pentane fraction was performed by GC. The GC analysis conditions of squalene are shown in the following Table 2, and the result of the GC analysis showed a peak of squalene at 30.7 min.

TABLE 2

| Item | Condition |
|---|---|
| GC model | Varian star 3400 cx |
| Column | 19091J-413 HP-5 (30 m × 0.32 mm × 0.25 μm) |
| Injection volume | 2 μl |
| Temperature | 40° C. 3 min, 10° C./min 240° C. 5 min, 10° C./min 300° C. 1 min |
| Time | 35 min |

Example 3

Overexpression Effects of HMG1 Gene on Squalene Productivity

Firstly, overexpression effects of the HMG1 gene, which is known to be the most important rate-determining step in the biosynthesis of isoprenoids such as squalene, on squalene productivity, were examined.

In order to examine the effect on squalene productivity according to the differences among the strains and the promoter activities of expression vectors therefrom, Saccharomyces cerevisiae Y2805 strain was used together with Saccharomyces cerevisiae W303 and YPH499 strains (Tokuhiro K. et al., Appl. Environ. Microbiol. 75, 5536-5543 (2009)) commonly used as host cells for gene expression, with combinations of the GAL10 promoter or the ADH1 promoter (Table 3).

TABLE 3

<Overexpression effects of HMG1 gene on squalene productivity>

| Strain | Vector | Squalene (g/l) | OD$_{600}$ | DCW (Dry cell weight, g/l) | Squalene (mg/g DCW) |
|---|---|---|---|---|---|
| Y2805 | — | 0.0032 | 29.1 | 8.47 | 0.4 |
| Y2805 | pGal-HMG1 | 0.450 | 21.6 | 6.26 | 71.9 |
| Y2805 | pADH1-HMG1 | 0.484 | 19.4 | 5.63 | 86.0 |
| W303 | — | 0.0001 | 21.1 | 6.12 | 0.0 |
| W303 | pGal-HMG1 | 0.006 | 14.3 | 4.15 | 1.4 |
| W303 | pADH1-HMG1 | 0.0012 | 19.0 | 5.51 | 0.2 |
| YPH499 | — | 0.0012 | 19.3 | 5.60 | 0.2 |
| YPH499 | pGal-HMG1 | 0.023 | 8.9 | 2.58 | 8.9 |
| YPH499 | pADH1-HMG1 | 0.092 | 11.7 | 3.39 | 27.1 |

As shown in Table 3, among the control groups having no HMG1 gene-overexpressing vector, the Y2805 strain showed a slightly higher productivity than other strains. The recombinant strains showed a great increase in the squalene productivity by overexpression of the HMG1 gene, and there were differences in the overexpression effects of the HMG1 gene among strains. The Y2805 strain showed a remarkable increase in squalene productivity, compared to the W303 or YPH strain. The Y2805 strain showed high productivities with both the GAL10 and ADH1 promoters. On the contrary, the YPH strain showed considerably low squalene productivity with the GAL10 promoter, compared to the ADH1 promoter. Meanwhile, the W303 strain showed very low productivities with both of the promoters.

Example 4

Overexpression Effects of Various Isoprenoid Biosynthetic Genes on Squalene Productivity The overexpression effects of various isoprenoid biosynthetic genes were examined using the Y2805 strain that showed a high squalene productivity in Example 3 (Table 4). In the control Y2805 strain expressing no isoprenoid biosynthetic genes, squalene was hardly detected. As is known, overexpression of the HMG1 gene greatly increased squalene productivity. However, the MVAE gene, which is an enzyme producing acetoacetyl CoA at the early stage of the squalene synthetic pathway and has functions overlapped with those of the HMG1 gene, showed no overexpression effects. Co-expression of the MVAE gene with other genes showed negative effects on productivity. Single overexpression of the GPPS gene, which produces GPP (geranyl pyrophosphate) as the precursor of squalene, showed no effects. Co-expression of the GPP gene with the HMG1 gene showed lower productivity than single overexpression of the HMG1 gene.

Single overexpression of the ispA and Erg20 genes, which are FPP synthase genes producing FPP (farnesyl pyrophosphate) as the immediate precursor of squalene, showed no effects on squalene production, which is an unpredicted result, considering the previous study of increasing the productivity of prenyl alcohols up to 5-6 fold by overexpression of the ispA gene in *E. coli* (Ohto C. et al., Biosci. Biotechnol. Biochem. 73, 186-188 (2009)). This result suggests that *E. coli* and yeast utilize non-mevalonate and mevalonate pathways, respectively and the control mechanisms of the genes are different from each other.

Meanwhile, co-overexpression of the ispA and Erg20 genes with the HMG1 gene remarkably increased squalene productivity, and showed approximately two-fold higher productivity over a single overexpression of the HMG1 gene. In addition, *E. coli*-derived ispA gene showed more excellent effects than yeast-derived Erg20 gene.

The results of Table 4, taken together, suggest that as the combinations of two or more genes of the squalene biosynthetic pathway unpredictably showed an increase or decrease in the squalene production, attempts of various gene combinations are needed.

TABLE 4

<Overexpression effects of isoprenoid biosynthetic genes on squalene productivity in *Saccharomyces cerevisiae* 2805 strain>

| | Strain Vector | Squalene (g/l) | OD$_{600}$ | DCW (Dry cell weight, g/l) | Squalene (mg/g DCW) |
|---|---|---|---|---|---|
| 1 | — | 0.003 | 29.1 | 8.47 | 0.4 |
| 2 | pGal-HMG1 | 0.492 | 31.0 | 8.98 | 54.8 |
| 3 | pGal-MVAE | 0.003 | 19.5 | 5.64 | 0.5 |
| 4 | pGal-ispA | 0.001 | 34.4 | 9.96 | 0.1 |
| 5 | pGal-ispA/HMG1 | 1.246 | 30.0 | 8.69 | 143.4 |
| 6 | pGal-ispA/MVAE | 0.005 | 33.5 | 9.70 | 0.5 |
| 7 | pGal-GPPS | 0.002 | 28.1 | 8.15 | 0.2 |
| 8 | pGal-GPPS/HMG1 | 0.114 | 33.3 | 9.66 | 11.8 |
| 9 | pGal-GPPS/MVAE | 0.004 | 34.8 | 10.08 | 0.4 |
| 10 | pGal-Erg20 | 0.004 | 36.5 | 10.60 | 0.4 |
| 11 | pGal-Erg20/HMG1 | 0.886 | 35.6 | 10.31 | 85.9 |

The ispA/HMG1 combination showing the most excellent squalene productivity in the results of Table 4 was used to examine its effects on squalene productivity in the Y2805 strain and several other *Saccharomyces cerevisiae* strains that have been recently reported to show excellent isoprenoid productivity (Table 5).

TABLE 5

<Co-overexpression effects of HMG1 and ispA genes on squalene productivity according to yeast strain>

| Strain | Vector | Squalene (g/l) | OD$_{600}$ | DCW (Dry cell weight, g/l) | Squalene (mg/g DCW) |
|---|---|---|---|---|---|
| Y2805 | — | 0.0032 | 29.1 | 8.47 | 0.4 |
| Y2805 | Isp/HMG1 | 1.004 | 36.9 | 10.69 | 93.9 |
| ATCC201741 | — | 0.0008 | 17.0 | 4.93 | 0.2 |
| ATCC201741 | Isp/HMG1 | 0.032 | 16.7 | 4.84 | 6.6 |
| ATCC201238 | — | 0.0003 | 18.6 | 5.39 | 0.1 |
| ATCC201238 | Isp/HMG1 | 0.001 | 9.75 | 2.83 | 0.4 |
| ATCC200589 | — | 0.0023 | 27.0 | 7.83 | 0.3 |
| ATCC200589 | Isp/HMG1 | 0.013 | 18.9 | 5.47 | 2.4 |

As shown in Table 5, the control strains having no ispA/HMG1 gene-overexpressing vector showed very low squalene production, whereas the recombinant strains having ispA/HMG1 gene-overexpressing vectors showed a remarkable increase of squalene production, but there are large differences among the strains. Among them, the Y2805 strain showed very high squalene productivity, compared to other strains selected from about 40 kinds of ATCC strains that have been recently reported to show high isoprenoid productivity. Therefore, these results indicate that the Y2805 strain of the present invention has an excellent productivity.

INDUSTRIAL APPLICABILITY

The modified yeast strain of the present invention is used to overcome many limitations of the current sources of squalene and to produce squalene as a raw material for cosmetics or medicine with high efficiency. It is also expected to lower the high price of squalene due to short supply and high production costs.

The invention claimed is:

1. A modified yeast strain that is capable of producing squalene, wherein the modified yeast strain exhibits increased activity of HMG-CoA reductase (hydroxymethylglutaryl CoA reductase) and increased activity of farnesyl pyrophosphate synthase, compared with the corresponding non-modified yeast strain and wherein the modified yeast strain has Accession Number KCTC 11577BP or KCTC 11578BP.

2. The modified yeast strain according to claim 1, wherein the strain is produced by the introduction of a vector expressing HMG-CoA reductase and farnesyl pyrophosphate synthase.

3. The modified yeast strain according to claim 1, wherein the yeast strain is *Saccharomyces cerevisiae*.

4. The modified yeast strain according to claim 3, wherein the yeast strain is *Saccharomyces cerevisiae* Y2805.

5. The modified yeast strain according to claim 1, wherein the HMG-CoA reductase is encoded by HMG1 gene.

6. The modified yeast strain according to claim 5, wherein the HMG1 gene is derived from *Saccharomyces cerevisiae*.

7. The modified yeast strain according to claim 1, wherein the farnesyl pyrophosphate synthase is encoded by ispA gene or Erg20 gene.

8. The modified yeast strain according to claim 7, wherein the ispA gene is derived from *E. coli* and the Erg20 gene is derived from *Saccharomyces cerevisiae*.

9. The modified yeast strain according to claim 2, wherein the vector further comprises a GAL10 promoter.

10. A method for the production of squalene comprising culturing of the modified yeast strain according to claim 1.

* * * * *